United States Patent [19]

Wright

[11] Patent Number: 4,923,983
[45] Date of Patent: May 8, 1990

[54] METHOD OF RESOLVING CIS 3-AMINO-4-[2-(2-FURYL)ETH-1-YL]-1-METHOXYCARBONYLMETHYL-AZETIDIN-2-ONE

[75] Inventor: Ian G. Wright, Greenwood, Ind.

[73] Assignee: Eli Lilly and Company, Indianapolis, Ind.

[21] Appl. No.: 386,664

[22] Filed: Jul. 31, 1989

[51] Int. Cl.$^5$ .................. C07D 250/08; C07C 59/255
[52] U.S. Cl. .................................... 540/363; 540/203; 562/585
[58] Field of Search ................ 540/363, 203; 562/585

[56] References Cited

U.S. PATENT DOCUMENTS 3,116,332  12/1963  Sullivan .............................. 562/585

OTHER PUBLICATIONS

Hatanaka et al., Tetrahedron Letters, 24(45), 1983, pp. 4837 to 4838.

Ault, Techniques and Experiments for Organic Chemistry (Boston, Allan and Pacon), 1979, pp. 236 to 237.

*Primary Examiner*—Mukund J. Shah
*Assistant Examiner*—E. L. Ward
*Attorney, Agent, or Firm*—Bernard J. Graves, Jr.; Leroy Whitaker

[57] ABSTRACT

Cis $\alpha\alpha/\beta\beta$-3-amino-[2-(2-furyl)eth-1-yl]-1-methoxycarbonylmethyl-azetidin-2-one is resolved via optically active tartaric acid.

1 Claim, No Drawings

METHOD OF RESOLVING CIS 3-AMINO-4-[2-(2-FURYL)ETH-1-YL]-1-METHOXYCARBONYLMETHYL-AZETIDIN-2-ONE

BACKGROUND OF THE INVENTION

An important clinical trial candidate, (6R,7S) 7-(R)-phenylglycylinamido-3-chloro-1-azabicyclo[4.2.0]-oct-2-en-8-on-2-carboxylic acid (loracarbef) may be synthesized by various routes. One of the more noteworthy total syntheses of loracarbef is that made possible by Evans and Sjogren, U.S. Pat. No. 4,665,171. The Evans and Sjogren methodology provides a chiral 2+2 (ketone plus imine) cycloaddition, and accordingly, entry to a wide variety of chiral cis β-lactams. However, the Evans and Sjogren methodology provides for the utilization of a chiral auxiliary of the formula

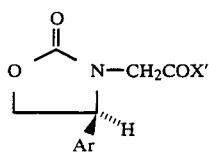

in the 2+2 cycloaddition with a Schiff's base, wherein X' is chloro, bromo, trifluoroacetoxy, or —OP(=)X₂, wherein X is halogen. The above chiral auxiliary is synthesized in seven steps from L-phenylglycine. The resulting cycloaddition provides compounds of the formula

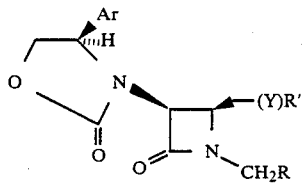

wherein Ar is phenyl, $C_1$-$C_4$ alkylphenyl, halophenyl, $C_1$-$C_4$ alkoxyphenyl, naphthyl, thienyl, furyl, benzothienyl, or benzofuryl; R is phenyl, $C_1$-$C_4$ alkylphenyl, $C_1$-$C_4$ alkoxyphenyl, or halophenyl; Y is —CH=CH—, or —CH₂—CH₂—; and R' is phenyl, $C_1$-$C_4$ alkylphenyl, $C_1$-$C_4$ alkoxyphenyl, halophenyl, furyl or naphthyl.

The obvious shortcomings of the Evans and Sjogren route are that a very expensive starting material, L-phenylglycine, is used, the chiral auxiliary is synthesized in several steps in linear fashion; and further, the chiral auxiliary is removed and discarded using Li/NH₃/t—C₄H₉OH to provide a free 3-amino-azetidinone.

As an achiral alternative, Hatanaka et al., Tetrahedron Letters Vol. 24, No. 49, pp 4837–4838 (1983), provides a method of preparing a 3-hydroxy(±)-1-carbacephalosporin via a 2+2 cycloaddition much in the same fashion as that of Evans and Sjogren, but without the use of a chiral auxiliary as the ketene source. The Hatanaka methodology provides many of the same intermediates as does the Evans and Sjogren synthesis, albeit in achiral form. The advantage of the achiral synthesis is economy of steps and starting material.

The present invention affords a useful alternative to the challenge of synthesizing chiral 1-carba(1-dethia)-cephalosporins by providing a method for resolution of a key achiral cis-azetidinone intermediate provided by achiral cis-2+2 cycloaddition. In particular, the present invention provides a method for resolution of an achiral intermediate in the total synthesis of 1-carba(1-dethia)-cephalsoporins using L-tartaric acid.

SUMMARY

Cis 3-amino-4-[2-(2-furyl)eth-1-yl]-1-methoxycarbonylmethyl-azetidin-2-one is resolved by the practice of this invention into its enantiomeric cis α,α and cis β,β components whereby the desired cis β,β enantiomer is selectively crystallized from solution using L-(+)-tartaric acid and seeds of the desired ββ-azetidinone enantiomer L-(+)-tartrate salt. The tartrate salt is obtained from the ββ-enantiomer which is obtained by resolution of the mixed enantiomers with S-(—)malic acid.

DESCRIPTION OF THE INVENTION

The present invention provides a method of resolving cis α,α/β,β azetidinone represented by the following two enantiomers:

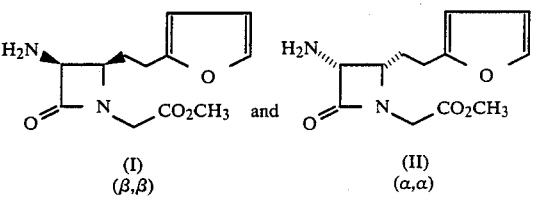

to yield optically pure isomers, each free of the other. This resolution is accomplished by dissolving a racemic mixture of I and II in a polar organic solvent, such as tetrahydrofuran or acetonitrile-water, and warming the solution to approximately 50° C. or at least a temperature sufficient to dissolve the racemate (I and II) and the malic acid. S(—)-malic acid is then added and the solutions allowed to cool gradually to room temperature overnight, thus forming the diastereomeric S(—)-malic acid salt of (I) in excellent yield and outstanding optical purity. This malate salt can then be used to generate a L-(+)-tartrate seed crystal for a resolution using L-tartaric acid as resolving acid as described below.

Thus, the present invention provides a method whereby inexpensive L-(+)-tartaric acid is used as a resolving agent in a solution I+II when seeded with crystals of the L-(+)-tartaric acid salt of (I) prepared from the resolved S-(—)-malic acid salt of (I). According to this method, a portion of a racemic mixture of (I) and (II) is dissolved in a polar organic solvent such as methanol, ethanol, 2-propanol, tetrahydrofuran, dimethoxyethane or acetonitrile in a concentration of about 0.25 molar to 1.0 molar and the solution is added to a concentrated solution of 0.5 to 0.6 equivalents of L-(+)-tartaric acid in water+(organic solvent of choice). Acetonitrile is the preferred solvent, and additionally, it contains water at a final concentration of 1-4%. Preferably the resulting solution is then seeded with crystals of the L-(+)-tartaric acid salt of (I). The resulting mixture is allowed to crystallize and the resulting L-(+)-tartaric acid salt of (I) is then collected. The resolved free amine can then be obtained by conventional methods.

The seed crystals of the L-(+)-tartaric acid salt of (I) are obtained originally by generating (I) from the resolved S-(—)-malic acid salt of (I) (copending application U.S. Ser. No. 07/258,919) using extraction into organic solvent such as ethyl acetate or methylene chloride from an aqueous solution made basic with sodium or potassium carbonate or bicarbonate. The extract of the resolved base is treated with one equivalent of L-(+)-tartaric acid under the conditions described to provide the crystalline tartrate salt.

Further, one could use the D-(−)-tartaric acid as resolving agent to obtain mother liquors enhanced in concentration of isomer (I), by removal of isomer (II)/D-(−)-tartrate solids.

As a further aspect of the present invention, in addition to the process for resolving the racemic mixture of (I) and (II) above, there is provided the L-(+)-tartaric acid salt of (I) and the D-(−)-tartaric acid salt of (II).

The diastereomeric salt formed can be separated from the resolution mixture and the free amino azetidinone recovered from the salt form by conventional methods. For example, the separated salt can be treated in an aqueous medium with a base to form the free amine which can be extracted from the aqueous phase with a water immiscible solvent such as ethyl acetate or methylene chloride. The process provides a high degree of separation of the two enantiomeric azetidinones as reflected by the observed enantiomeric excess (ee) of the product.

One skilled in the art will appreciate that the selective crystallization of one diastereomer from a polar organic solution is also affected by concentration. A relatively low concentration provides pure diastereomer of generally higher purity but lower yield, while the utilization of a higher concentration of racemate and resolving agent will normally provide higher yields of solid, many times at the expense of optical purity.

Further details of the above malic acid resolution can be found in copending application U.S. Ser. No. 07/258,919, incorporated herein by reference.

Thus, although L-(+)-tartaric acid was found to be inefficacious as an original resolution agent (as also reported in copending application U.S. Ser. No. 07/258,919), it may be utilized as a resolving agent if seeds of the desired L-(+)-tartaric acid salt of (I) are prepared from the resolved S-(−)-malic acid salt of (I). Further, once L-(+)-tartaric acid salts of (I) have been formed, such salts may in turn be used to "seed" further solutions of L-(+)-tartaric acid and (I)/(II) racemic mixtures to obtain L-(+)-tartaric acid salts of (I).

The invention is further described by the following examples but is not to be construed as limiting any aspect of the invention.

EXAMPLE 1

A 0.5 g portion of the oxalate salt of cis $\alpha\alpha/\beta\beta$, 3-amino-4-[2-(furyl)ethyl]-1-methoxycarbonylazetidin-2-one was slurried in 10 ml of water, neutralized to pH=7.5 with saturated NaHCO$_3$ solution and extracted with CH$_2$Cl$_2$. The CH$_2$Cl$_2$ solution was dried over anhydrous MgSO$_4$, filtered, and concentrated in vacuo to provide the racemic free-amine.

A 0.232 g sample of the resulting racemic free amine was then dissolved in tetrahydrofuran (2 ml) and heated to about 50° C. A 0.134 g portion of S(−)-malic acid was then added and the resulting solution was allowed to stand overnight.

The containing vessel was wrapped in insulation, thereby allowing the solution to gradually cool to room temperature. The resulting crystalline solid was then filtered and washed with 1 ml tetrahydrofuran to provide 40 mg (22% yield) of the S(−)-malic acid salt of cis $\beta,\beta$-3-amino-4-[2-(2-furyl)eth-1-yl]-1-methoxycarbonylmethyl-azetidin-2-one.

The L-malic salt (5 mg, 14 μm) was dissolved in a mixture of 1 ml H$_2$O, 3.5 mg (3 meq) NaHCO$_3$, and 1 ml acetonitrile and 3.2 mg (14 μm) of 3,5-dinitrobenzoyl chloride was added and the reaction stirred for 16 hr at room temperature. After 5 ml H$_2$O was added, the reaction was vacuum filtered and washed with H$_2$O (2×1 ml portions), cold isopropanol (2×1 ml portions) and diethyl ether (2×2 ml) to isolate 2.5 mg of the 3,5-dinitrobenzamide, "DBN", (85 area % by gradient reverse phase HPLC).

The amide solution in tetrahydrofuran was injected on both a YMC-AK03S-5300A, 25 cm, 4.6 mm OD chiral column (YMC Corporation) and a Pirkle covalent D-naphthylalanine chiral column (Regis) to show a 99% ee (enantiomeric excess). Also, the $\beta\beta$-DNB amide made from a chiral $\beta$-lactam made by the Evans and Sjogren route and the analogous racemic DNB amide was injected on both systems to confirm the retention times of both the $\beta\beta$- and the $\alpha\alpha$-DNB amides.

EXAMPLE 2

The procedure for isolation of the $\alpha,\alpha$ isomer was identical to that of Example 1, substituting R(+)-malic acid as resolving agent to provide the $\alpha,\alpha$ isomer (27% yield, 99% ee).

EXAMPLE 3

A 7.35 g (0.0291 mol) sample of cis-$\alpha,\alpha/\beta,\beta$-3-amino-4-[2-(2-furyl)eth-1-yl]-1-methoxycarbonylmethyl-azetidin-2-one was dissolved in 10 ml of CH$_3$CN and treated with 2.19 g (0.0146 mol) of L-(+)tartaric acid dissolved in 1.02 ml of water and 12 ml of warm CH$_3$CN. An additional 7.1 ml of CH$_3$CN was used as rinse. The above mixture was then heated to 35° C. and seeded with the L-(+)-tartaric acid salt of the cis $\beta\beta$ azetidinone.

The solution was then allowed to cool overnight and filtered. Yield: 4.23 g (72.3%) m.p.=142.0°–143.0° C. 89.2% enantiomeric excess.

EXAMPLES 4–22

Examples 4 through 22 illustrate the optimum results for the process of the present invention.

|   | CH$_3$CN L/mol | % H$_2$O | Equiv. L-(+)-tartaric acid | Isolate at °C. | % Yield Calc. from free base | M.P. °C. | Enantiomeric excess of $\beta\beta$ isomer |
|---|---|---|---|---|---|---|---|
| 4 | 3.0 | 2.0 | 0.50 | 25 | 91.0 | 134.0–6.0 | 65.6 |
| 5 | 3.0 | 3.0 | 0.50 | 25 | 80.1 | 139.5–40.5 | 81.0 |
| 6 | 3.0 | 3.5 | 0.50 | 25 | 75.1 | 141.5–2.0 | 86.6 |
| 7 | 0.8 | 4.0 | 0.50 | 25 | 68.1 | 143.0–4.0 | 92.2 |
| 8 | 1.0 | 4.0 | 0.50 | 25 | 70.5 | 142.5–3.5 | 91.4 |

-continued

|    | CH₃CN L/mol | % H₂O | Equiv. L-(+)-tartaric acid | Isolate at °C. | % Yield Calc. from free base | M.P. °C. | Enantiomeric excess of ββ isomer |
|----|------|-----|------|-----|------|-----------|------|
| 9  | 1.0  | 4.5 | 0.50 | 25  | 66.7 | 144.0–4.5 | 95.4 |
| 10 | 1.5  | 4.0 | 0.50 | 25  | 71.5 | 142.5–3.0 | 90.4 |
| 11 | 2.0  | 4.0 | 0.50 | 25  | 70.9 | 142.5–3.0 | 92.4 |
| 12 | 2.5  | 4.0 | 0.50 | 25  | 71.3 | 143.0–3.5 | 91.4 |
| 13 | 3.0  | 4.0 | 0.50 | 25  | 71.1 | 142.5–3.5 | 92.0 |
| 14 | 3.0  | 4.0 | 0.50 | −10 | 71.3 | 142.0–3.0 | 92.0 |
| 15 | 4.0  | 2.0 | 0.50 | 25  | 87.9 | 135.5–7.0 | 70.4 |
| 16 | 3.0  | 3.5 | 0.55 | 25  | 78.8 | 140.5–1.0 | 83.6 |
| 17 | 2.0  | 4.0 | 0.55 | 25  | 74.9 | 141.5–2.0 | 86.6 |
| 18 | 2.5  | 4.0 | 0.55 | 25  | 75.1 | 141.0–1.5 | 87.4 |
| 19 | 3.0  | 4.0 | 0.55 | 25  | —    | 140.5–1.0 | 88.0 |
| 20 | 3.0  | 4.0 | 0.55 | 25  | 74.2 | 141.2–1.7 | 88.4 |
| 21 | 3.0  | 4.0 | 0.55 | −10 | 75.5 | 140.5–1.0 | 87.4 |
| 22 | 3.0  | 4.0 | 0.60 | 25  | 76.5 | 141.0–1.5 | 86.6 |

We claim:

1. A method for resolving cis αα/ββ-3-amino-4-[2-(2-furyl)eth-1-yl]-methoxycarbonylmethyl-azetidin-2-one into its component enantiomers, which comprises the steps:

(a) contacting a solution of acetonitrile containing between 1 and 4% water and the cis αα/ββ racemate with at least about 0.5 mole-equivalents of an optically active tartaric acid;

(b) seeding said solution with an optically-active L-(+)-tartaric acid salt of cis ββ-3-amino-4-[2-(2-furyl)eth-1-yl]-1-methoxycarbonylmethyl-1-azetidin-2-one or the D-(−) tartaric acid salt of cis αα-3-amino-4-[2-(2-furyl)eth-1-yl]-1-methoxycarbonylmethyl-1-azetidin-2-one; and (c) separating the insoluble salt formed thereby.

* * * * *